(12) United States Patent
Baumann et al.

(10) Patent No.: US 12,186,115 B2
(45) Date of Patent: Jan. 7, 2025

(54) METHOD FOR MOVING A PATIENT COUCH

(71) Applicant: Siemens Healthcare GmbH, Erlangen (DE)

(72) Inventors: Berthold Baumann, Kastl (DE); Gerhard Wurzer, Mantel (DE); Alexander Kraemer, Irchenrieth (DE)

(73) Assignee: Siemens Healthineers AG, Forchheim (DE)

( * ) Notice: Subject to any disclaimer, the term of this patent is extended or adjusted under 35 U.S.C. 154(b) by 219 days.

(21) Appl. No.: 17/867,895

(22) Filed: Jul. 19, 2022

(65) Prior Publication Data

US 2023/0029121 A1 Jan. 26, 2023

(30) Foreign Application Priority Data

Jul. 23, 2021 (EP) .................................. 21187402

(51) Int. Cl.
| | |
|---|---|
| *A61B 5/00* | (2006.01) |
| *A61B 6/00* | (2006.01) |
| *A61B 6/04* | (2006.01) |

(52) U.S. Cl.
CPC ............ *A61B 6/0487* (2020.08); *A61B 5/704* (2013.01); *A61B 6/54* (2013.01)

(58) Field of Classification Search
CPC .......... A61B 5/704; A61B 6/54; A61B 6/0487
See application file for complete search history.

(56) References Cited

U.S. PATENT DOCUMENTS

| | | |
|---|---|---|
| 2005/0031080 A1 | 2/2005 | Klingenbeck-Regn et al. |
| 2009/0144902 A1* | 6/2009 | Baumann ............ A61B 6/0487 700/60 |
| 2013/0315381 A1 | 11/2013 | Dong |
| 2017/0007196 A1 | 1/2017 | Don et al. |
| 2017/0325759 A1 | 11/2017 | Teramoto et al. |
| 2019/0302712 A1* | 10/2019 | Neti .................. G05B 23/0254 |
| 2020/0330055 A1* | 10/2020 | Talgorn ................... A61B 6/04 |
| 2022/0165410 A1 | 5/2022 | Schmidt et al. |

FOREIGN PATENT DOCUMENTS

| | | |
|---|---|---|
| DE | 19809738 A1 | 9/1999 |
| DE | 10333295 A1 | 2/2005 |
| DE | 102020214654 A1 | 5/2022 |
| EP | 2675359 A1 | 12/2013 |
| JP | 2002058667 A | 2/2002 |
| JP | 2009000209 A | 1/2009 |
| WO | WO 2015081295 A1 | 6/2015 |
| WO | WO 2021094391 A1 | 5/2021 |

* cited by examiner

*Primary Examiner* — Joel F Brutus
(74) *Attorney, Agent, or Firm* — Harness, Dickey & Pierce, P.L.C.

(57) ABSTRACT

The method includes: providing a body value of a patient; setting an operating parameter of a drive chain via a control unit configured to control the drive chain as a function of the body value in such a manner that a speed value of the patient couch is increased and a rocking of the patient couch during the movement of the patient couch is at least partially suppressed; and moving the patient couch via the drive chain in accordance with the increased speed value to perform the medical imaging.

20 Claims, 5 Drawing Sheets

METHOD FOR MOVING A PATIENT COUCH

CROSS-REFERENCE TO RELATED APPLICATION(S)

The present application claims priority under 35 U.S.C. § 119 to European Patent Application No. 21187402.9, filed Jul. 23, 2021, the entire contents of which are incorporated herein by reference.

FIELD

One or more embodiments of the present invention relate to a method for moving a patient couch as a function of a body value of a patient positioned on the patient couch for medical imaging, the associated patient couch and the associated computer program product.

BACKGROUND

Movement of a conventional patient couch within a recording region of an imaging modality typically takes place independently of the patient positioned on the patient couch. The movement of the conventional patient couch regularly takes place without the patient being digitally detected in advance and the movement being adapted to the patient. The conventional patient couch and the conventional drive chain thereof are in particular designed for a maximum example of an exemplary patient. In particular, the maximum example may comprise a mass value of 300 or 400 kg. The movement of the conventional patient couch typically takes place at an invariable maximum speed, which is specified in accordance with this mass value.

An X-ray diagnostic facility with an X-ray emitter, a control apparatus connected thereto, a detector and a patient positioning table is known from DE 103 33 295 A1, wherein the X-ray diagnostic facility has an apparatus, which calculates the body mass index from the body length and the weight of the patient to be examined, and wherein the apparatus is connected to the control apparatus for the purpose of influencing parameters that determine the X-ray radiation.

DE 198 09 738 A1 discloses an X-ray diagnostic device, in particular for a digital chest X-ray unit, with a control unit for presetting the collimator setting required for a recording, which is provided with a computing unit which, on the basis of patient-related data, makes a calculation with regard to a preset adapted to the patient, wherein the control unit is provided with direct access to the patient data and contains an organ program memory with standard values for the collimator setting, in order to ascertain the size of the organ, or a body region to be examined, from the patient-related data and to set the optimum collimator value in a motorized manner.

WO 2015/081 295 A1 describes a system and a method for improving projection-based and tomographic X-ray imaging, which comprise a depth detection device for measuring a depth of at least one body part of the patient via the depth detection device and a control unit for calculating a thickness and/or a circumference of the body part, using the depth information. The calculated thickness and/or circumference information is used to ascertain an optimum level of X-ray dose for the body part. The system and the method also comprise a camera for identifying the body part which is to be examined, and for detecting any movement of the identified body part.

WO 2021/094 391 A1 discloses a control system for controlling an imaging device, which comprises an electronic control unit with a control memory and a control display. The electronic control unit is connected to control the imaging device during operation and is programmed to store a control state in the control memory; to execute imaging device setup software, so that the electronic control unit provides a setup user interface on the electronic control unit, by which a user configures the control state in the control memory; and to execute control software, so that the electronic control unit controls the imaging device for acquisition of images in accordance with the control state stored in the control memory.

DE 10 2020 214 654.3, which has not yet been published, describes remote communication with a medical technology facility with the aid of a digital twin, wherein the remote control facility has a data detection unit for detecting state data and machine data of a medical technology facility, an evaluation unit for generating a digital twin on the basis of the state data and machine data, a display unit for displaying the digital twin and a control unit for actuating the medical technology facility on the basis of the displayed data of the digital twin.

SUMMARY

One or more embodiments of the present invention disclose a method for moving a patient couch as a function of a body value of a patient positioned on the patient couch for medical imaging, the associated patient couch and the associated computer program product, so that the drive chain of the patient couch is controlled on a patient-dependent and state-dependent basis.

A method, according to one or more embodiments of the present invention, for moving a patient couch as a function of a body value of a patient positioned on the patient couch for medical imaging, wherein the medical imaging takes place in an imaging modality with a recording region, wherein the patient couch can be moved within the recording region via a drive chain, comprises the following steps:
  providing a body value, in particular a mass and/or physique, of the patient,
  setting an operating parameter of the drive chain via a control unit for controlling the drive chain as a function of the body value in such a manner that a speed value of the patient couch is increased and a rocking of the patient couch during the movement of the patient couch is at least partially suppressed, and
  moving the patient couch via the drive chain in accordance with the increased speed value to perform the medical imaging.

The method according to one or more embodiments of the present invention has, in particular, the following advantages:

Taking into consideration the body value, in particular the mass and/or the physique, of the patient advantageously makes it possible to move the patient couch on a patient-specific basis. The patient-specific movement preferably takes place in a different manner for a short, obese patient and a tall, slim patient, for example, wherein the two patients usually influence the patient couch and the drive chain thereof differently due to mass inertia.

The rocking of the patient couch being at least partially suppressed makes it possible to increase the image quality. The increase in the speed value preferably makes it possible to move the patient couch more quickly. The quicker movement of the patient couch offers the advantage of an increased patient throughput. The increased speed value may be advantageous in particular during the examination of an emergency patient.

Furthermore, an examination duration of the medical imaging advantageously may be reduced, which usually increases the convenience for the patient. The quicker movement may additionally lead to an increase in image quality, for example because an image quality-reducing influence caused by respiration and/or another movement of the patient is less likely, the shorter the examination duration.

The imaging modality may be a magnetic resonance tomography unit, a computed tomography unit, an angiography system, an X-ray fluoroscopy facility, a positron emission tomography unit or a combination of the modalities mentioned above. The imaging modality is embodied for performing the medical imaging. The imaging modality may additionally be embodied for radiotherapy or particle therapy.

Each imaging modality has a recording region, in which the patient is situated for the performing of the medical imaging. Depending on the type of the medical imaging and/or the imaging modality, an extent of the recording region and/or the examination duration typically varies.

The patient couch according to one or more embodiments of the present invention shares the advantages described previously, is embodied for moving a positioned patient and has a couch board for positioning of the patient,
a drive chain for moving the patient couch and
a control unit for controlling the drive chain.

The positioning of the patient on the patient couch typically corresponds to the positioning of the patient on the couch board.

The movement of the patient couch may comprise an absolute movement of the patient couch together with the drive chain, so that the patient couch can be moved as a unit in the recording region via the drive chain, for example. For example, the patient couch may have a displaceable platform, on which the couch board and the drive chain are arranged. In this case, the drive chain is able to move the displaceable platform and thus the patient couch.

As an alternative or in addition, the movement of the patient couch may comprise a relative movement of the couch board in relation to the drive chain and/or in relation to the platform of the patient couch. In this case, the platform may itself additionally be displaceable.

The patient typically lies still on the patient couch while the patient couch is being moved and/or the medical imaging is being performed. A blanket and/or a belt may support the stabilization of the patient.

Typically, the patient is positioned on the patient couch at a distance from the imaging modality, outside the recording region, and is then displaced into the recording region for the performing of the medical imaging, by the patient couch being moved with the patient positioned on the patient couch. In particular, the movement of the patient couch corresponds to a displacement of the patient couch. The patient couch with the patient may be moved into the recording region on one side and moved out on the other side. It is conceivable for the patient couch to be moved entirely out of the recording region on the one side and/or on the other side. In principle, the movement of the patient couch may take place in all three spatial axes in relation to the recording region. A sideways movement of the patient couch is not regularly provided. The patient couch typically carries out a lifting and/or horizontal movement. When the patient couch carries out the lifting movement and the horizontal movement, there is typically an oblique movement.

The drive chain has drive device or mechanism for moving the patient couch within the recording region. The drive device or mechanism may comprise a drive train, wheels, a motor and/or a gear unit. The drive chain is typically additionally able to move the patient couch outside the recording region. The patient couch, in particular the platform of the patient couch, is typically in contact with the floor via the wheels.

According to one or more embodiments of the present invention, the body value is the mass of the patient or the physique of the patient or a tuple of the mass and the physique. In the latter case, the mass and the physique are therefore body values of the patient. In particular, the mass of the patient corresponds to a weight of the patient. In particular, the physique of the patient describes a body length of the patient, a proportion of the patient, an outline of the patient and/or a positioning of the patient on the patient couch. In particular, the physique corresponds to a mass distribution of the mass of the patient on the patient couch.

The body value is, in particular, a biometric feature of the patient. The body value may be designated an index of the patient. The body value typically differs between the patient and another patient. The movement of the patient couch with the patient differs from a movement of the patient couch with the other patient, due to the mass inertia for example, the influence of which on the rocking regularly depends upon the mass and/or the physique of the two patients.

The provision of the body value of the patient comprises, in particular, the provision of the mass and/or physique. The provision may comprise a detecting of the body value and/or a storing of the body value and/or a retrieving of the body value. The body value may be temporarily stored in a memory unit. The body value can be retrieved from the memory unit. The provision of the body value can take place via an interface. The provision of the body value may comprise a transferring of the body value to the control unit of the drive chain.

The body value may be detected, for example, via a sensor before the positioning or after the positioning of the patient on the patient couch. The body value may be provided in a patient file. The detection may take place via a camera, in particular a stereoscopic and/or thermal imaging camera. In principle, it is conceivable to detect the body value via a weighing apparatus and/or from an operating state of the patient couch which is adapted to the patients and the therefore additional body value. In this case, the operating state may map a motor torque of the drive chain, which is varied due to a friction that can be assigned to the positioning of the patient, which makes it possible to detect the body value from a body value-friction model, for example.

The operating parameter of the drive chain influences the operation of the drive chain. The operation of the drive chain varies as a function of a variation of the operating parameter. In particular, the operating parameter controls the operation of the drive chain. The operation of the drive chain and/or the operating parameters may be variable over time, in particular dynamically regulated.

The setting of the operating parameter typically takes place in the control unit. The control unit is embodied for controlling the drive chain in particular by way of the setting of the operating parameter. In particular, the control unit has control program code for the setting of the operating parameter. As an alternative or in addition, the control unit may have an analog circuit for the setting of the operating parameter. The control unit may be part of the drive chain or the patient couch. In principle, it is conceivable for the control unit to be arranged outside the patient couch. The setting of the operating parameter may take place via a wired connection or wirelessly. The control unit may comprise an interface for the transferring of the operating parameter and/or the drive chain may comprise an interface for the receiving of the operating parameter. The setting of the operating parameter may comprise a transferring and/or a drive chain-side receiving.

The setting of the operating parameter may take place multiple times, in particular in a clocked manner, preferably repeatedly. The setting of the operating parameter takes place as a function of the body value in such a manner that the operating parameter depends upon the body value. Typically, the operating parameter additionally depends upon an operating state of the patient couch. In particular, the setting of the operating parameter takes place as a function of the body value and the operating state of the patient couch. In particular, the operating state may depend upon the operating parameter and/or vice versa.

In particular, the speed value of the patient couch is increased compared to a previous speed value before the increase. As an alternative or in addition, the speed value of the patient couch may be increased compared to a standard speed value for a conventional patient. In principle, it is conceivable for the speed value of the patient couch to be increased compared to a resonance speed value, which describes a resonance speed with a certain probability of the rocking. It is a further possibility that the speed value of the patient couch is increased compared to a speed value of another patient.

The operating parameter is approximately set in such a manner that the speed value is higher, the shorter and/or slimmer the patient. In particular, the speed value comprises the speed and/or the acceleration. Advantageously, the operating parameter is set as a function of the body value in such a manner that the speed value is increased up to a maximum value. The maximum value of the speed value may be predefined by a power limit of the drive chain. Alternatively, the maximum value of the speed value may correspond to a threshold value that depends upon the body value, in order to prevent the patient from slipping and/or lifting up. In another case, the maximum value of the speed value may be predefined by a user of the patient couch. In particular, the control unit is configured to set the operating parameter in such a manner that the speed value is only increased up to the maximum value. In principle, it is conceivable that, when increasing the speed value, in particular for comfort and/or wear and/or safety reasons, the maximum value is (only) pushed to 50%, for example 80% or 90%, so that a power reserve up to a maximum value remains intact. During the lifting movement, the maximum value may amount to more than 10 mm/s and/or less than 100 mm/s, in particular 50 mm/s, for example. During the horizontal movement, the maximum value may amount to more than 50 mm/s and/or less than 1000 mm/s, in particular 500 mm/s, for example.

A rocking that is not suppressed may become apparent in what is known as a wobbling of the patient, in particular of soft parts of the patient. In particular, the suppression of the rocking of the patient couch comprises the suppression of the rocking of the patient positioned on the patient couch. In particular, the suppression of the rocking corresponds to preventing the patient couch from progressively starting to vibrate. In particular, the suppression of the rocking comprises damping the vibration. For example, the rocking is suppressed by the patient couch being moved more quickly or more slowly in relation to the resonance speed at which the rocking would occur and/or is probable. The rocking regularly occurs at the resonance speed. The suppression of the rocking therefore may require an increasing of the distance from the resonance speed. In principle, it may be the case that the rocking is more probable, the higher the speed value. As an alternative or in addition, the rocking can be suppressed, for example, by the patient couch being less intensely or more intensely accelerated in accordance with the speed value. In particular, the suppression of the rocking takes place only in part and thus does not entirely exclude a certain residual vibration. The residual vibration may lie below a threshold value in relation to a non-suppressed rocking, for example.

The suppression of the rocking typically requires a comprehensive, that is to say systemic viewing of the patient couch and the patient positioned on the patient couch, because the patient couch and the patient are clearly moved together via the drive chain. For the suppression of the rocking, in particular the body value and the operating state of the patient couch are taken into consideration.

In particular, the setting of the operating parameter comprises a re-adaptation of the operating parameter and/or a regulation of the drive chain during the movement of the patient couch, so that the rocking is at least partially suppressed during the movement of the patient couch. The regulation of the drive chain usually comprises a monitoring and/or detecting of the operating state and/or an actual speed value that is predefined in accordance with the increased speed value and/or the compliance with the set operating parameter. In a case where a set operating parameter does not at least partially suppress the rocking of the patient couch during the movement of the patient couch, the control unit may set the operating parameter once again. For this, an adjustment of the operating state may be necessary. The setting of the operating parameter may take place repeatedly on an ongoing basis during the movement of the patient couch. "During the movement of the patient couch" in particular comprises the period of time after the patient couch has initially come to a standstill and before the following time the patient couch comes to a standstill, during which the patient couch is moved. Alternatively or in addition, "during the movement of the patient couch" comprises the period of time of the examination duration.

The patient couch is moved via the drive chain in such a manner that the medical imaging of the patient can be performed. In this context, the patient couch is moved in particular in the direction of the recording region and/or into the recording region and/or through the recording region. The movement of the patient couch takes place in accordance with the increased speed value. During the movement of the patient couch, the control unit is preferably able to regulate the drive chain and/or set the operating parameter.

One embodiment provides that, before the setting of the operating parameter, at least one sequence parameter of an imaging protocol, in accordance with which the medical imaging is performed, is retrieved and wherein the operating parameter is set in accordance with the at least one sequence parameter. This embodiment is advantageous in particular because the type of the medical imaging can be taken into consideration during the movement of the patient couch. For example, a certain imaging protocol, which provides the imaging of a physiology of the patient and/or a contrast agent enhancement in the patient, can be performed at all or with an improved image quality. The consideration of the sequence parameter when setting the operating parameter, while simultaneously suppressing the rocking, advantageously makes it possible to move the patient couch on an imaging protocol-dependent and patient-dependent basis. If the operating parameter is set in accordance with the at least one sequence parameter, the speed value can be increased more intensely as a function of the sequence parameter, for example through the use of the power reserve. The at least one sequence parameter may be provided, in particular transferred, by the imaging modality for retrieval, for example. The retrieval may take place by way of the control unit, for example. The control unit may have an interface for the retrieval of the at least one sequence parameter.

One embodiment provides that the at least one sequence parameter provides a movement of the patient couch within the recording region. This embodiment is advantageous in particular because as a result the movement of the patient couch provided in accordance with the at least one sequence parameter can be taken into consideration when setting the operating parameter. The consideration may take place in the form of a relative reduction or amplification of the increase in the speed value.

One embodiment provides that the provided movement comprises at least one change in direction. A change in direction is defined by a directed movement axis, along which the patient couch is moved, being changed. For example, a change in direction is present if the patient couch carries out a lifting movement and subsequently a horizontal movement, or vice versa. During a change in direction, in particular the influence of the mass inertia on the rocking is especially significant, so that the rocking may differ for different patients. The non-suppressed rocking is typically more probable, the greater the change in direction. This embodiment offers the advantage in particular that this influence, which is significant for the at least one change in direction, can be taken into consideration when setting the operating parameter.

One embodiment provides that the at least one change in direction amounts to 180°. A change in direction by 180° is referred to as zig-zag, for example. A change in direction of this kind typically leads to the patient couch being moved back and forth, in particular initially along the directed movement axis and subsequently along a movement axis that is antiparallel in relation to the directed movement axis. At least one imaging protocol provides a change in direction of this kind, in order for example to preferably examine a region to be examined, which is larger than the recording region, of the patient multiple times. A plurality of changes in direction during the movement of the patient couch regularly amount to 180°. It is particularly advantageous if the operating parameter is set in accordance with the at least one change in direction and the rocking is at least partially suppressed.

One embodiment provides that the setting of the operating parameter comprises selecting a motor current characteristic curve of the drive chain as a function of the body value. Typically, the motor current predefined by the motor current characteristic curve, which is consumed in the drive chain, correlates with the speed value. In particular, the motor current characteristic curve correlates with a motor torque provided by the drive chain for the movement of the patient couch. The motor current characteristic curve may be provided with further motor current characteristic curves for selection in a memory unit, for example. The control unit typically selects the motor current characteristic curve, in particular as a function of the body value and the patient couch.

One embodiment provides that the speed value predefines an acceleration ramp of the patient couch and/or a maximum speed of the patient couch. The acceleration ramp may provide an increasing of the speed and/or a reducing of the speed for braking the patient couch. In particular, the acceleration ramp depends upon the acceleration. The maximum speed of the patient couch typically correlates with the maximum value of the speed value. The operating parameter may, for example, initially set the acceleration ramp and subsequently set the maximum speed of the patient couch.

One embodiment provides that the increased speed value corresponding to the operating parameter to be set is provided on a display unit for a user of the patient couch. For example, the display unit may comprise a screen, in particular may be designed as part of a smartphone or a tablet. This embodiment is advantageous in particular because the body value-dependent speed value is displayed to the user. The user can enable the operating parameter to be set, in particular, for the movement of the patient couch. In principle, it is conceivable for the user to be able to adapt the operating parameter to be set via a switch unit, when the increased speed value is displayed to the user for enabling before the movement of the patient couch. As an alternative or in addition, the user is able to adapt the maximum value of the speed value via the switch unit, for example, when the operating parameter to be set exceeds the previously set maximum value. The switch unit may comprise a rotary knob for setting in a stepless manner.

One embodiment provides that the body value is detected before the patient is positioned on the patient couch. This embodiment is advantageous in particular because the operating parameter can already be set before the patient is positioned on the patient couch.

One embodiment provides that the body value is entered into a digital twin of the drive chain of the patient couch, wherein the digital twin digitally maps at least one operating state of the drive chain of the patient couch which influences the operating parameter and, as a function of the entered body value and the mapped operating state, ascertains the operating parameter for the setting. The digital twin is additionally able to digitally map the patient couch and/or the patient. This embodiment is particularly advantageous as a possibility for the comprehensive, that is to say systemic viewing of the patient couch and the patient positioned on the patient couch. In particular, the digital twin offers the advantage that it is typically able to simulate and/or model the movement of the patient couch at least in an approximate manner. The digital twin maps forces, motor torques, load scenarios, deformations and/or frictions, which act in and on the drive chain and/or patient couch, at least in part, preferably entirely, in the operating state. The entering of the body value may take place by way of the control unit. In principle, it is conceivable for the digital twin to comprise an interface for receiving the body value. The digital twin is typically mapped in program code, which can be executed in a computing unit. The computing unit may be part of the control unit. The ascertaining of the operating parameter may comprise the simulation and/or the modeling of the movement of the patient couch, wherein an output parameter of the simulation and/or the modeling is the operating parameter provided for the setting. Included in the operating state are, in particular, the body value, the mass and/or the physique, of the patient, the state of the drive chain and/or the state of the patient couch. The state of the drive chain and/or the state of the patient couch may map a function of the respective elements, for example the drive device or mechanism, and/or the operating times thereof and/or the maintenance intervals thereof and/or the deformations thereof on the basis of the positioned patient.

One embodiment provides that, before the ascertaining of the operating parameter, the at least one operating state influencing the operating parameter is adapted to the body value. This embodiment is advantageous in particular because the ascertaining of the operating parameter may take place on a prospective basis.

One embodiment provides that, after the movement of the patient couch, the operating state is adapted to the wear experienced due to the movement of the patient couch in such a manner that a friction value is increased. In particular, this embodiment offers the advantage that the digital twin is updated on the basis of the movement of the patient couch and it is therefore possible to once again set an operating parameter more precisely for a further movement of the patient couch. The wear can be ascertained, for example, through the simulation and/or modeling of the movement of the patient couch and/or can be detected via a wear sensor. Usually, the wear is caused by the movement of the patient couch, which typically leads to higher friction, which is mapped in the friction value.

One embodiment provides that the digital twin is operated in a cloud computing facility. The access of the digital twin to the interface of the control unit for the transferring of the ascertained operating parameter and/or the access of the control unit to the digital twin for entering the body value typically takes place via a computer network. The cloud computing facility may be operated in a cloud server. In principle, it is conceivable for part of the cloud server to be designed as control unit.

The computer program product, according to one or more embodiments of the present invention, which can be loaded directly into a memory of a computing unit, has program code in order to carry out the method when the computer program product is executed in the computing unit.

The computer program product may be a computer program or comprise a computer program. In particular, the computer program product has the program code which map the method steps according to one or more embodiments of the present invention. As a result, the method according to one or more embodiments of the present invention can be carried out in a defined and repeatable manner, and control can be exercised over a dissemination of the method according to one or more embodiments of the present invention. The computer program product is preferably configured in such a manner that the computing unit can carry out the method steps according to one or more embodiments of the present invention via the computer program product. In particular, the program code can be loaded into a memory of the computing unit and typically can be executed via a processor of the computing unit with access to the memory. If the computer program product, in particular the program code, is executed in the computing unit, typically all embodiments of the method described can be performed. The computer program product is, for example, saved on a physical, computer-readable medium and/or stored digitally as a data packet in a computer network. The computer program product may represent the physical, computer-readable medium and/or the data packet in the computer network. One or more embodiments of the present invention can thus also start from the physical, computer-readable medium and/or the data packet in the computer network. The physical, computer-readable medium can usually be connected directly to the computing unit, for example in that the physical, computer-readable medium is inserted into a DVD drive or into a USB port, whereby the computing unit can access the physical, computer-readable medium, in particular with read access. The data packet can preferably be retrieved from the computer network. The computer network may have the computing unit or be connected to the processing unit and/or control unit indirectly via a wide area network (WAN) connection and/or via a (wireless) local area network (WLAN or LAN) connection. For example, the computer program product may be stored digitally on a cloud server at a storage location of the computer network, and be transferred via the WAN via the Internet and/or via the WLAN or LAN to the computing unit, in particular by following a download link that points to the storage location of the computer program product.

Features, advantages or alternative embodiments mentioned in the description of the apparatus are also transferable similarly to the method and vice versa. In other words, claims for the method can be developed with features of the apparatus and vice versa. In particular, the apparatus according to one or more embodiments of the present invention can be used in the method.

BRIEF DESCRIPTION OF THE DRAWINGS

The present invention will now be described and explained in greater detail making reference to the exemplary embodiments illustrated in the figures. In principle, structures and units which remain essentially the same are identified in the following description of the figures with the same reference characters as on the first occurrence of the relevant structure or unit.

In the drawings.

DETAILED DESCRIPTION

A method, according to one or more embodiments of the present invention, for moving a patient couch as a function of a body value of a patient positioned on the patient couch for medical imaging, wherein the medical imaging takes place in an imaging modality with a recording region, wherein the patient couch can be moved within the recording region via a drive chain, comprises the following steps:

providing a body value, in particular a mass and/or physique, of the patient, setting an operating parameter of the drive chain via a control unit for controlling the drive chain as a function of the body value in such a manner that a speed value of the patient couch is increased and a rocking of the patient couch during the movement of the patient couch is at least partially suppressed, and moving the patient couch via the drive chain in accordance with the increased speed value to perform the medical imaging.

The imaging modality may be a magnetic resonance tomography unit, a computed tomography unit, an angiography system, an X-ray fluoroscopy facility, a positron emission tomography unit or a combination of the modalities mentioned above. The imaging modality is embodied for performing the medical imaging. The imaging modality may additionally be embodied for radiotherapy or particle therapy.

Each imaging modality has a recording region, in which the patient is situated for the performing of the medical imaging. Depending on the type of the medical imaging and/or the imaging modality, an extent of the recording region and/or the examination duration typically varies.

The patient couch according to one or more embodiments of the present invention shares the advantages described previously, is embodied for moving a positioned patient and has a couch board for positioning of the patient,
a drive chain for moving the patient couch and
a control unit for controlling the drive chain.

The positioning of the patient on the patient couch typically corresponds to the positioning of the patient on the couch board.

The movement of the patient couch may comprise an absolute movement of the patient couch together with the drive chain, so that the patient couch can be moved as a unit in the recording region via the drive chain, for example. For example, the patient couch may have a displaceable platform, on which the couch board and the drive chain are arranged. In this case, the drive chain is able to move the displaceable platform and thus the patient couch.

As an alternative or in addition, the movement of the patient couch may comprise a relative movement of the couch board in relation to the drive chain and/or in relation to the platform of the patient couch. In this case, the platform may itself additionally be displaceable.

The patient typically lies still on the patient couch while the patient couch is being moved and/or the medical imaging is being performed. A blanket and/or a belt may support the stabilization of the patient.

Typically, the patient is positioned on the patient couch at a distance from the imaging modality, outside the recording region, and is then displaced into the recording region for the performing of the medical imaging, by the patient couch being moved with the patient positioned on the patient couch. In particular, the movement of the patient couch corresponds to a displacement of the patient couch. The patient couch with the patient may be moved into the recording region on one side and moved out on the other side. It is conceivable for the patient couch to be moved entirely out of the recording region on the one side and/or on the other side. In principle, the movement of the patient couch may take place in all three spatial axes in relation to the recording region. A sideways movement of the patient couch is not regularly provided. The patient couch typically carries out a lifting and/or horizontal movement. When the patient couch carries out the lifting movement and the horizontal movement, there is typically an oblique movement.

The drive chain has drive device or mechanism for moving the patient couch within the recording region. The drive device or mechanism may comprise a drive train, wheels, a motor and/or a gear unit. The drive chain is typically additionally able to move the patient couch outside the recording region. The patient couch, in particular the platform of the patient couch, is typically in contact with the floor via the wheels.

According to one or more embodiments of the present invention, the body value is the mass of the patient or the physique of the patient or a tuple of the mass and the physique. In the latter case, the mass and the physique are therefore body values of the patient. In particular, the mass of the patient corresponds to a weight of the patient. In particular, the physique of the patient describes a body length of the patient, a proportion of the patient, an outline of the patient and/or a positioning of the patient on the patient couch. In particular, the physique corresponds to a mass distribution of the mass of the patient on the patient couch.

The body value is, in particular, a biometric feature of the patient. The body value may be designated an index of the patient. The body value typically differs between the patient and another patient. The movement of the patient couch with the patient differs from a movement of the patient couch with the other patient, due to the mass inertia for example, the influence of which on the rocking regularly depends upon the mass and/or the physique of the two patients.

The provision of the body value of the patient comprises, in particular, the provision of the mass and/or physique. The provision may comprise a detecting of the body value and/or a storing of the body value and/or a retrieving of the body value. The body value may be temporarily stored in a memory unit. The body value can be retrieved from the memory unit. The provision of the body value can take place via an interface. The provision of the body value may comprise a transferring of the body value to the control unit of the drive chain.

The body value may be detected, for example, via a sensor before the positioning or after the positioning of the patient on the patient couch. The body value may be provided in a patient file. The detection may take place via a camera, in particular a stereoscopic and/or thermal imaging camera. In principle, it is conceivable to detect the body value via a weighing apparatus and/or from an operating state of the patient couch which is adapted to the patients and the therefore additional body value. In this case, the operating state may map a motor torque of the drive chain, which is varied due to a friction that can be assigned to the positioning of the patient, which makes it possible to detect the body value from a body value-friction model, for example.

The operating parameter of the drive chain influences the operation of the drive chain. The operation of the drive chain varies as a function of a variation of the operating parameter. In particular, the operating parameter controls the operation of the drive chain. The operation of the drive chain and/or the operating parameters may be variable over time, in particular dynamically regulated.

The setting of the operating parameter typically takes place in the control unit. The control unit is embodied for controlling the drive chain in particular by way of the setting of the operating parameter. In particular, the control unit has control program code for the setting of the operating parameter. As an alternative or in addition, the control unit may have an analog circuit for the setting of the operating parameter. The control unit may be part of the drive chain or the patient couch. In principle, it is conceivable for the control unit to be arranged outside the patient couch. The setting of the operating parameter may take place via a wired connection or wirelessly. The control unit may comprise an interface for the transferring of the operating parameter and/or the drive chain may comprise an interface for the receiving of the operating parameter. The setting of the operating parameter may comprise a transferring and/or a drive chain-side receiving.

The setting of the operating parameter may take place multiple times, in particular in a clocked manner, preferably repeatedly. The setting of the operating parameter takes place as a function of the body value in such a manner that the operating parameter depends upon the body value. Typically, the operating parameter additionally depends upon an operating state of the patient couch. In particular, the setting of the operating parameter takes place as a function of the body value and the operating state of the patient couch. In particular, the operating state may depend upon the operating parameter and/or vice versa.

In particular, the speed value of the patient couch is increased compared to a previous speed value before the increase. As an alternative or in addition, the speed value of the patient couch may be increased compared to a standard speed value for a conventional patient. In principle, it is conceivable for the speed value of the patient couch to be increased compared to a resonance speed value, which describes a resonance speed with a certain probability of the rocking. It is a further possibility that the speed value of the patient couch is increased compared to a speed value of another patient.

The operating parameter is approximately set in such a manner that the speed value is higher, the shorter and/or slimmer the patient. In particular, the speed value comprises the speed and/or the acceleration. Advantageously, the operating parameter is set as a function of the body value in such a manner that the speed value is increased up to a maximum value. The maximum value of the speed value may be predefined by a power limit of the drive chain. Alternatively, the maximum value of the speed value may correspond to a threshold value that depends upon the body value, in order to prevent the patient from slipping and/or lifting up. In another case, the maximum value of the speed value may be predefined by a user of the patient couch. In particular, the control unit is configured to set the operating parameter in such a manner that the speed value is only increased up to the maximum value. In principle, it is conceivable that, when increasing the speed value, in particular for comfort and/or wear and/or safety reasons, the maximum value is (only) pushed to 50%, for example 80% or 90%, so that a power reserve up to a maximum value remains intact. During the lifting movement, the maximum value may amount to more than 10 mm/s and/or less than 100 mm/s, in particular 50 mm/s, for example. During the horizontal movement, the maximum value may amount to more than 50 mm/s and/or less than 1000 mm/s, in particular 500 mm/s, for example.

A rocking that is not suppressed may become apparent in what is known as a wobbling of the patient, in particular of soft parts of the patient. In particular, the suppression of the rocking of the patient couch comprises the suppression of the rocking of the patient positioned on the patient couch. In particular, the suppression of the rocking corresponds to preventing the patient couch from progressively starting to vibrate. In particular, the suppression of the rocking comprises damping the vibration. For example, the rocking is suppressed by the patient couch being moved more quickly or more slowly in relation to the resonance speed at which the rocking would occur and/or is probable. The rocking regularly occurs at the resonance speed. The suppression of the rocking therefore may require an increasing of the distance from the resonance speed. In principle, it may be the case that the rocking is more probable, the higher the speed value. As an alternative or in addition, the rocking can be suppressed, for example, by the patient couch being less intensely or more intensely accelerated in accordance with the speed value. In particular, the suppression of the rocking takes place only in part and thus does not entirely exclude a certain residual vibration. The residual vibration may lie below a threshold value in relation to a non-suppressed rocking, for example.

The suppression of the rocking typically requires a comprehensive, that is to say systemic viewing of the patient couch and the patient positioned on the patient couch, because the patient couch and the patient are clearly moved together via the drive chain. For the suppression of the rocking, in particular the body value and the operating state of the patient couch are taken into consideration.

In particular, the setting of the operating parameter comprises a re-adaptation of the operating parameter and/or a regulation of the drive chain during the movement of the patient couch, so that the rocking is at least partially suppressed during the movement of the patient couch. The regulation of the drive chain usually comprises a monitoring and/or detecting of the operating state and/or an actual speed value that is predefined in accordance with the increased speed value and/or the compliance with the set operating parameter. In a case where a set operating parameter does not at least partially suppress the rocking of the patient couch during the movement of the patient couch, the control unit may set the operating parameter once again. For this, an adjustment of the operating state may be necessary. The setting of the operating parameter may take place repeatedly on an ongoing basis during the movement of the patient couch. "During the movement of the patient couch" in particular comprises the period of time after the patient couch has initially come to a standstill and before the following time the patient couch comes to a standstill, during which the patient couch is moved. Alternatively or in addition, "during the movement of the patient couch" comprises the period of time of the examination duration.

The patient couch is moved via the drive chain in such a manner that the medical imaging of the patient can be performed. In this context, the patient couch is moved in particular in the direction of the recording region and/or into the recording region and/or through the recording region. The movement of the patient couch takes place in accordance with the increased speed value. During the movement of the patient couch, the control unit is preferably able to regulate the drive chain and/or set the operating parameter.

One embodiment provides that, before the setting of the operating parameter, at least one sequence parameter of an imaging protocol, in accordance with which the medical imaging is performed, is retrieved and wherein the operating parameter is set in accordance with the at least one sequence parameter. This embodiment is advantageous in particular because the type of the medical imaging can be taken into consideration during the movement of the patient couch. For example, a certain imaging protocol, which provides the imaging of a physiology of the patient and/or a contrast agent enhancement in the patient, can be performed at all or with an improved image quality. The consideration of the sequence parameter when setting the operating parameter, while simultaneously suppressing the rocking, advantageously makes it possible to move the patient couch on an imaging protocol-dependent and patient-dependent basis. If the operating parameter is set in accordance with the at least one sequence parameter, the speed value can be increased more intensely as a function of the sequence parameter, for example through the use of the power reserve. The at least one sequence parameter may be provided, in particular transferred, by the imaging modality for retrieval, for example. The retrieval may take place by way of the control unit, for example. The control unit may have an interface for the retrieval of the at least one sequence parameter.

One embodiment provides that the at least one sequence parameter provides a movement of the patient couch within the recording region. This embodiment is advantageous in particular because as a result the movement of the patient couch provided in accordance with the at least one sequence parameter can be taken into consideration when setting the operating parameter. The consideration may take place in the form of a relative reduction or amplification of the increase in the speed value.

One embodiment provides that the provided movement comprises at least one change in direction. A change in direction is defined by a directed movement axis, along which the patient couch is moved, being changed. For example, a change in direction is present if the patient couch carries out a lifting movement and subsequently a horizontal movement, or vice versa. During a change in direction, in particular the influence of the mass inertia on the rocking is especially significant, so that the rocking may differ for different patients. The non-suppressed rocking is typically more probable, the greater the change in direction. This embodiment offers the advantage in particular that this influence, which is significant for the at least one change in direction, can be taken into consideration when setting the operating parameter.

One embodiment provides that the at least one change in direction amounts to 180°. A change in direction by 180° is referred to as zig-zag, for example. A change in direction of this kind typically leads to the patient couch being moved back and forth, in particular initially along the directed movement axis and subsequently along a movement axis that is antiparallel in relation to the directed movement axis. At least one imaging protocol provides a change in direction of this kind, in order for example to preferably examine a region to be examined, which is larger than the recording region, of the patient multiple times. A plurality of changes in direction during the movement of the patient couch regularly amount to 180°. It is particularly advantageous if the operating parameter is set in accordance with the at least one change in direction and the rocking is at least partially suppressed.

One embodiment provides that the setting of the operating parameter comprises selecting a motor current characteristic curve of the drive chain as a function of the body value. Typically, the motor current predefined by the motor current characteristic curve, which is consumed in the drive chain, correlates with the speed value. In particular, the motor current characteristic curve correlates with a motor torque provided by the drive chain for the movement of the patient couch. The motor current characteristic curve may be provided with further motor current characteristic curves for selection in a memory unit, for example. The control unit typically selects the motor current characteristic curve, in particular as a function of the body value and the patient couch.

One embodiment provides that the speed value predefines an acceleration ramp of the patient couch and/or a maximum speed of the patient couch. The acceleration ramp may provide an increasing of the speed and/or a reducing of the speed for braking the patient couch. In particular, the acceleration ramp depends upon the acceleration. The maximum speed of the patient couch typically correlates with the maximum value of the speed value. The operating parameter may, for example, initially set the acceleration ramp and subsequently set the maximum speed of the patient couch.

One embodiment provides that the increased speed value corresponding to the operating parameter to be set is provided on a display unit for a user of the patient couch. For example, the display unit may comprise a screen, in particular may be designed as part of a smartphone or a tablet. This embodiment is advantageous in particular because the body value-dependent speed value is displayed to the user. The user can enable the operating parameter to be set, in particular, for the movement of the patient couch. In principle, it is conceivable for the user to be able to adapt the operating parameter to be set via a switch unit, when the increased speed value is displayed to the user for enabling before the movement of the patient couch. As an alternative or in addition, the user is able to adapt the maximum value of the speed value via the switch unit, for example, when the operating parameter to be set exceeds the previously set maximum value. The switch unit may comprise a rotary knob for setting in a stepless manner.

One embodiment provides that the body value is detected before the patient is positioned on the patient couch. This embodiment is advantageous in particular because the operating parameter can already be set before the patient is positioned on the patient couch.

One embodiment provides that the body value is entered into a digital twin of the drive chain of the patient couch, wherein the digital twin digitally maps at least one operating state of the drive chain of the patient couch which influences the operating parameter and, as a function of the entered body value and the mapped operating state, ascertains the operating parameter for the setting. The digital twin is additionally able to digitally map the patient couch and/or the patient. This embodiment is particularly advantageous as a possibility for the comprehensive, that is to say systemic viewing of the patient couch and the patient positioned on the patient couch. In particular, the digital twin offers the advantage that it is typically able to simulate and/or model the movement of the patient couch at least in an approximate manner. The digital twin maps forces, motor torques, load scenarios, deformations and/or frictions, which act in and on the drive chain and/or patient couch, at least in part, preferably entirely, in the operating state. The entering of the body value may take place by way of the control unit. In principle, it is conceivable for the digital twin to comprise an interface for receiving the body value. The digital twin is typically mapped in program code, which can be executed in a computing unit. The computing unit may be part of the control unit. The ascertaining of the operating parameter may comprise the simulation and/or the modeling of the movement of the patient couch, wherein an output parameter of the simulation and/or the modeling is the operating parameter provided for the setting. Included in the operating state are, in particular, the body value, the mass and/or the physique, of the patient, the state of the drive chain and/or the state of the patient couch. The state of the drive chain and/or the state of the patient couch may map a function of the respective elements, for example the drive device or mechanism, and/or the operating times thereof and/or the maintenance intervals thereof and/or the deformations thereof on the basis of the positioned patient.

One embodiment provides that, before the ascertaining of the operating parameter, the at least one operating state influencing the operating parameter is adapted to the body value. This embodiment is advantageous in particular because the ascertaining of the operating parameter may take place on a prospective basis.

One embodiment provides that, after the movement of the patient couch, the operating state is adapted to the wear experienced due to the movement of the patient couch in such a manner that a friction value is increased. In particular, this embodiment offers the advantage that the digital twin is updated on the basis of the movement of the patient couch and it is therefore possible to once again set an operating parameter more precisely for a further movement of the patient couch. The wear can be ascertained, for example, through the simulation and/or modeling of the movement of the patient couch and/or can be detected via a wear sensor. Usually, the wear is caused by the movement of the patient couch, which typically leads to higher friction, which is mapped in the friction value.

One embodiment provides that the digital twin is operated in a cloud computing facility. The access of the digital twin to the interface of the control unit for the transferring of the ascertained operating parameter and/or the access of the control unit to the digital twin for entering the body value typically takes place via a computer network. The cloud computing facility may be operated in a cloud server. In principle, it is conceivable for part of the cloud server to be designed as control unit.

The computer program product, according to one or more embodiments of the present invention, which can be loaded directly into a memory of a computing unit, has program code in order to carry out the method when the computer program product is executed in the computing unit.

The computer program product may be a computer program or comprise a computer program. In particular, the computer program product has the program code which map the method steps according to one or more embodiments of the present invention. As a result, the method according to one or more embodiments of the present invention can be carried out in a defined and repeatable manner, and control can be exercised over a dissemination of the method according to one or more embodiments of the present invention. The computer program product is preferably configured in such a manner that the computing unit can carry out the method steps according to one or more embodiments of the present invention via the computer program product. In particular, the program code can be loaded into a memory of the computing unit and typically can be executed via a processor of the computing unit with access to the memory. If the computer program product, in particular the program code, is executed in the computing unit, typically all embodiments of the method described can be performed. The computer program product is, for example, saved on a physical, computer-readable medium and/or stored digitally as a data packet in a computer network. The computer program product may represent the physical, computer-readable medium and/or the data packet in the computer network. One or more embodiments of the present invention can thus also start from the physical, computer-readable medium and/or the data packet in the computer network. The physical, computer-readable medium can usually be connected directly to the computing unit, for example in that the physical, computer-readable medium is inserted into a DVD drive or into a USB port, whereby the computing unit can access the physical, computer-readable medium, in particular with read access. The data packet can preferably be retrieved from the computer network. The computer network may have the computing unit or be connected to the processing unit and/or control unit indirectly via a wide area network (WAN) connection and/or via a (wireless) local area network (WLAN or LAN) connection. For example, the computer program product may be stored digitally on a cloud server at a storage location of the computer network, and be transferred via the WAN via the Internet and/or via the WLAN or LAN to the computing unit, in particular by following a download link that points to the storage location of the computer program product.

Figure 1:
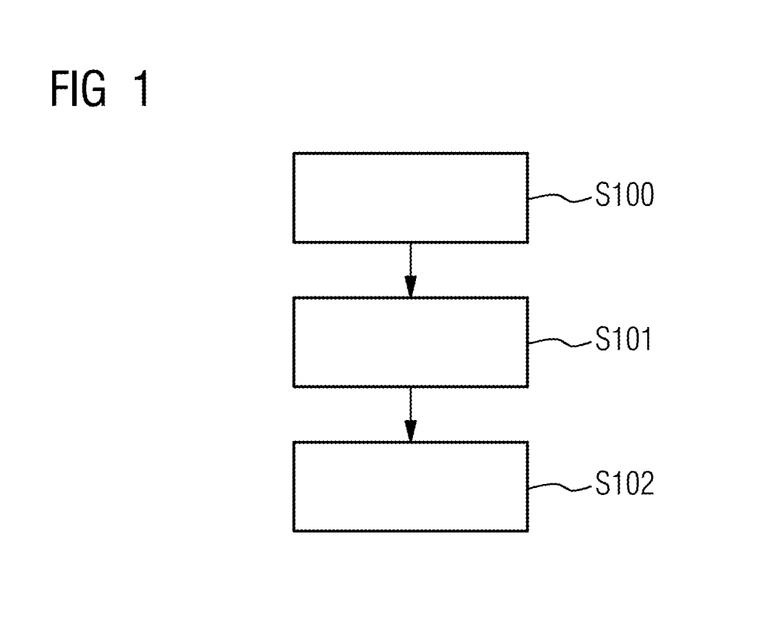
FIG. 1 shows a method, according to one or more embodiments of the present invention, for moving a patient couch as a function of a body value of a patient positioned on the patient couch for medical imaging.

FIG. 1 shows a method for moving a patient couch as a function of a body value of a patient positioned on the patient couch for medical imaging, wherein the medical imaging takes place in an imaging modality with a recording region, wherein the patient couch can be moved within the recording region via a drive chain, in a flow diagram with steps S100 to S102:

Method step S100 characterizes providing a body value, in particular a mass and/or physique, of the patient.

Method step S101 characterizes setting an operating parameter of the drive chain via a control unit for controlling the drive chain as a function of the body value in such a manner that a speed value of the patient couch is increased and a rocking of the patient couch during the movement of the patient couch is at least partially suppressed.

Method step S102 characterizes moving the patient couch via the drive chain in accordance with the increased speed value to perform the medical imaging.

Figure 2:
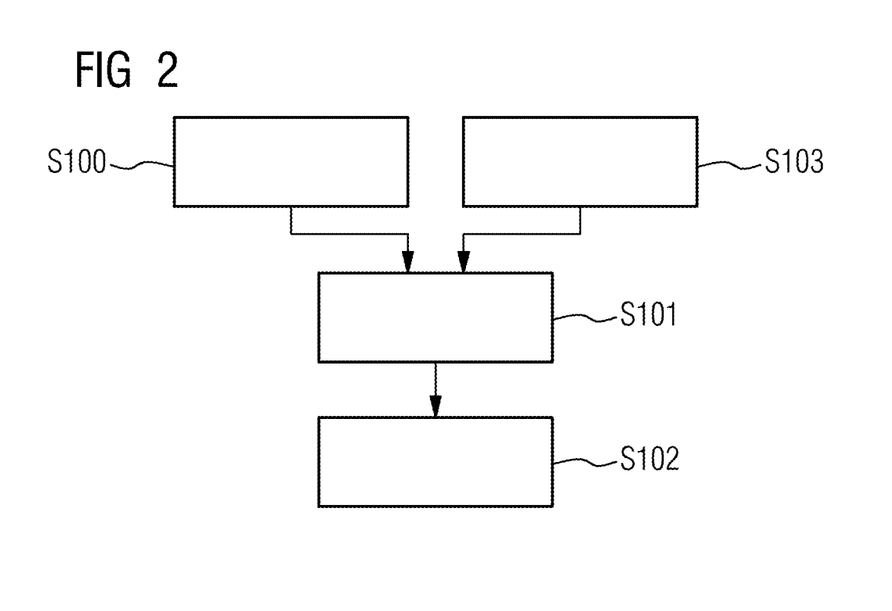
FIG. 2 shows a first exemplary embodiment of the method.

FIG. 2 shows a first exemplary embodiment of the method shown in FIG. 1 in a flow diagram:

Method step S103 characterizes that, before the setting of the operating parameter, at least one sequence parameter of an imaging protocol, in accordance with which the medical imaging is performed, is retrieved and wherein the operating parameter is set in accordance with the at least one sequence parameter.

Figure 3:
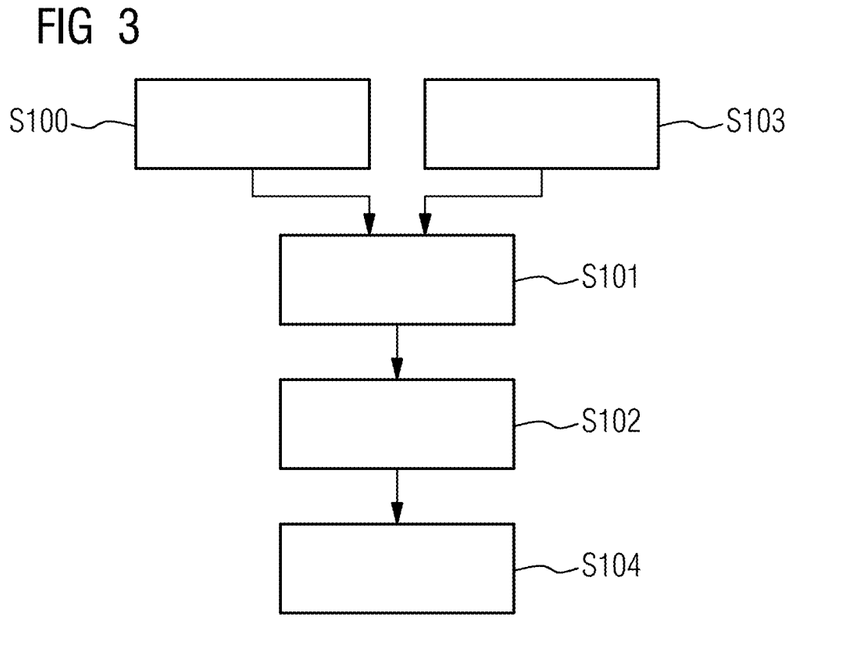
FIG. 3 shows a second exemplary embodiment of the method.

FIG. 3 shows a second exemplary embodiment of the method shown in FIG. 2 in a flow diagram:

Method step S104 characterizes that the at least one sequence parameter provides a movement of the patient couch within the recording region.

In particular, this embodiment may be developed in that the provided movement comprises at least one change in direction, in particular wherein the at least one change in direction amounts to 180°.

Figure 4:
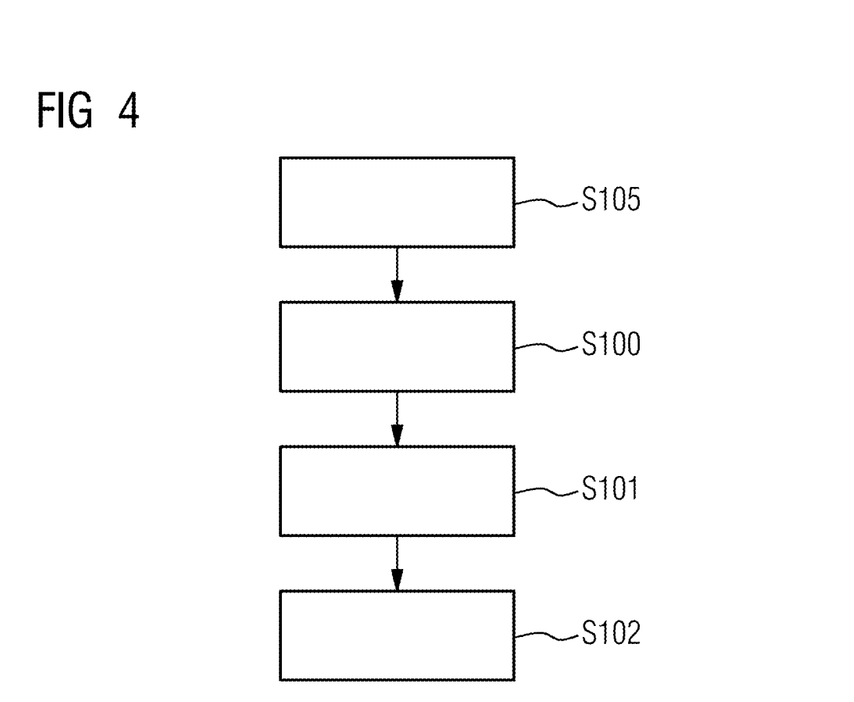
FIG. 4 shows a third exemplary embodiment of the method.

FIG. 4 shows a third exemplary embodiment of the method shown in FIG. 1 in a flow diagram:

Method step S105 characterizes that the body value is detected before the patient is positioned on the patient couch.

Figure 5:
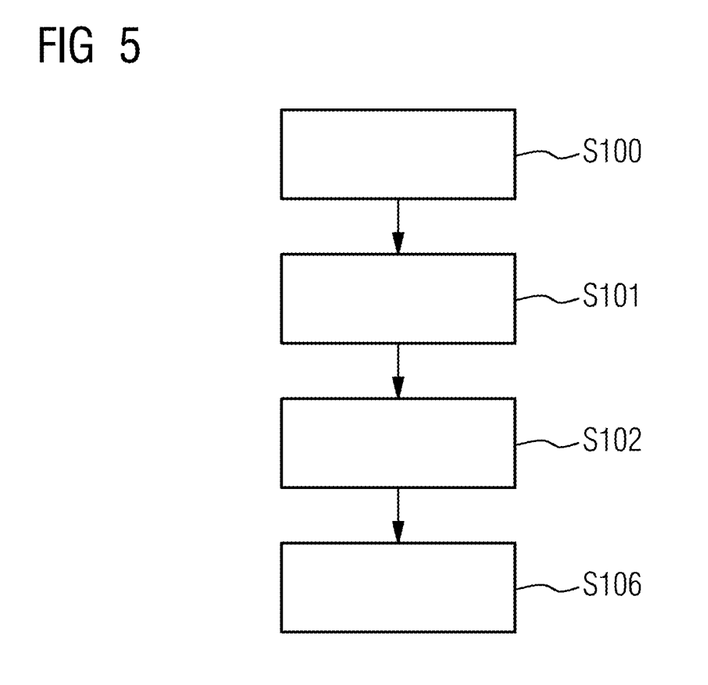
FIG. 5 shows a fourth exemplary embodiment of the method.

FIG. 5 shows a fourth exemplary embodiment of the method shown in FIG. 1 in a flow diagram:

Method step S106 characterizes that the increased speed value corresponding to the operating parameter to be set is provided on a display unit for a user of the patient couch.

Figure 6:
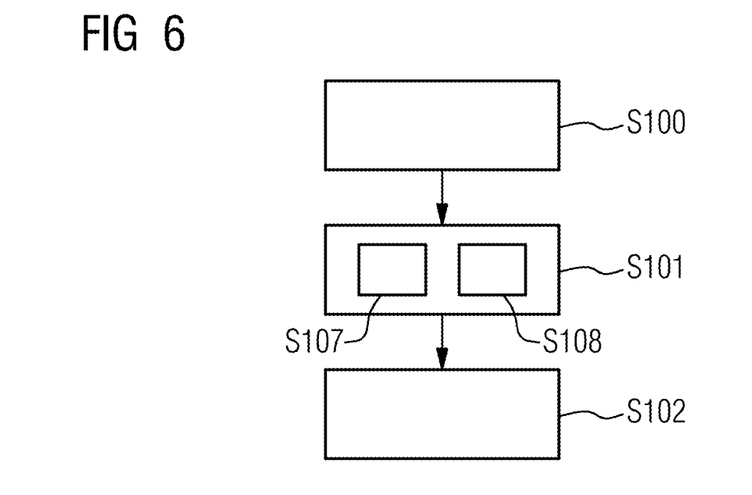
FIG. 6 shows a fifth exemplary embodiment of the method.

FIG. 6 shows a fifth exemplary embodiment of the method shown in FIG. 1 in a flow diagram:

Method step S107 characterizes that the setting of the operating parameter comprises selecting a motor current characteristic curve of the drive chain as a function of the body value.

The alternative or additional method step S108 characterizes that the speed value predefines an acceleration ramp of the patient couch and/or a maximum speed of the patient couch.

Figure 7:
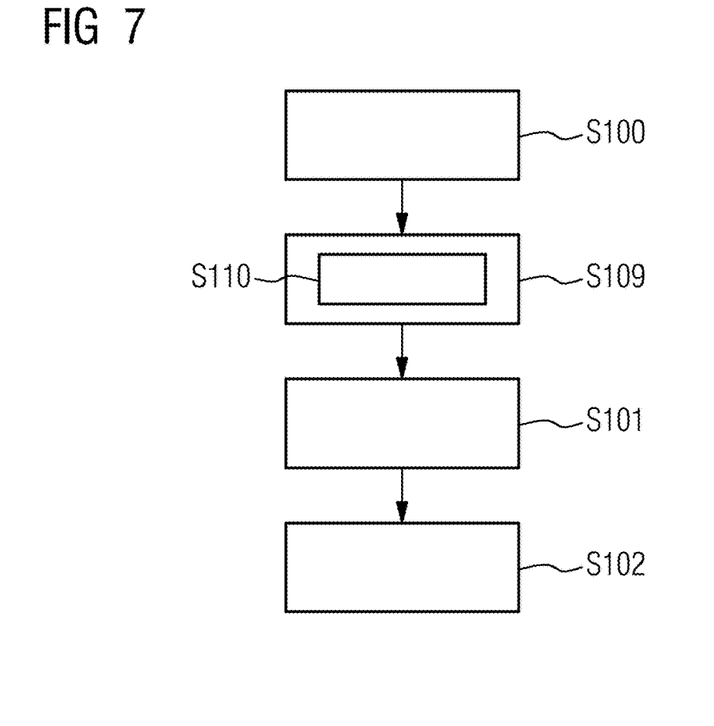
FIG. 7 shows a sixth exemplary embodiment of the method.

FIG. 7 shows a sixth exemplary embodiment of the method shown in FIG. 1 in a flow diagram:

Method step S109 characterizes that the body value is entered into a digital twin of the drive chain of the patient couch, wherein the digital twin digitally maps at least one operating state of the drive chain of the patient couch which influences the operating parameter and, as a function of the entered body value and the mapped operating state, ascertains the operating parameter for the setting.

An optional method step S110 characterizes that, before the ascertaining of the operating parameter, the at least one operating state influencing the operating parameter is adapted to the body value.

In principle, it is conceivable for the digital twin to be operated in a cloud computing facility.

Figure 8:
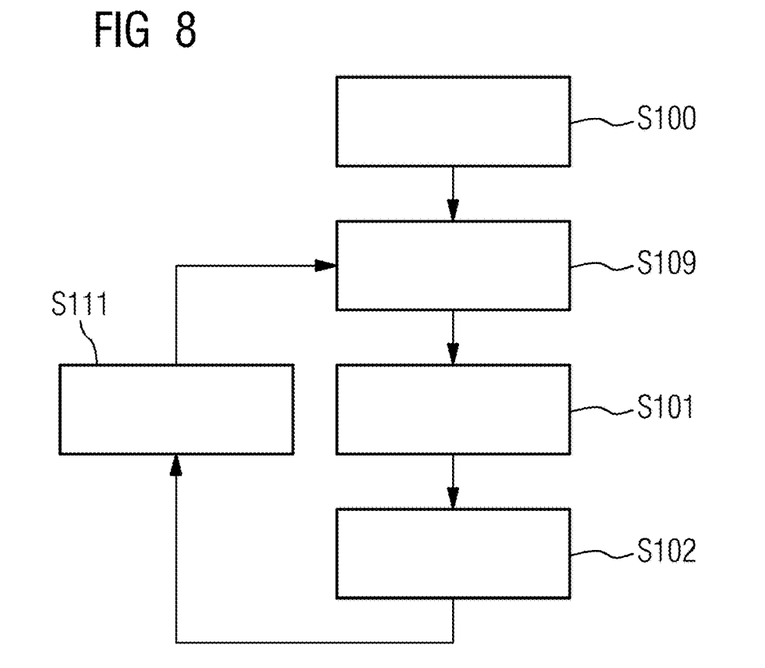
FIG. 8 shows a seventh exemplary embodiment of the method.

FIG. 8 shows a seventh exemplary embodiment of the method shown in FIG. 7 in a flow diagram:

Method step S111 characterizes that, after the movement of the patient couch, the operating state is adapted to the wear experienced due to the movement of the patient couch in such a manner that a friction value is increased.

Figure 9:
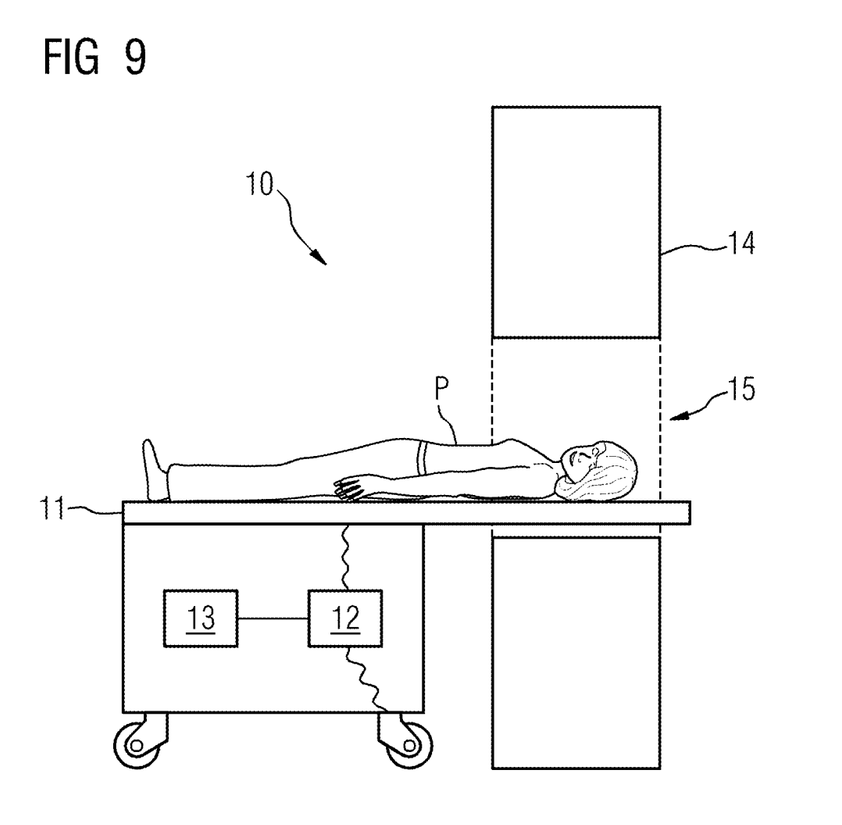
FIG. 9 shows a patient couch according to one or more embodiments of the present invention.

FIG. 9 shows the patient couch 10 according to one or more embodiments of the present invention. The patient couch 10 is embodied for moving a patient P positioned on it. The patient couch 10 has a couch board 11, a drive chain 12 and a control unit 13.

The couch board 11 is embodied for positioning of the patient P. The couch board is typically flat and elongated. In particular, the couch board 11 can be moved horizontally and/or vertically in relation to a floor, on which the patient couch 10 is standing.

The drive chain 12 is embodied for moving the patient couch 10. In particular, the drive chain 12 is able to move the patient couch 10 on an absolute basis, i.e. together with the drive chain 12 in relation to a position on the floor, and/or on a relative basis, i.e. in particular the couch board 11 in relation to the drive chain 12.

The control unit 13 is embodied for controlling the drive chain 12. For this purpose, the control unit is in particular connected to the drive chain 12 and/or the patient couch 10 and/or the couch board 11. In this exemplary embodiment, the control unit 13 is designed as part of the patient couch 10, so that it 13 is arranged on the platform of the patient couch 10 together with the drive chain 12.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects.

Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been illustrated and described in detail by the preferred exemplary embodiments, the present invention is nevertheless not restricted by the examples given and other variations can be derived therefrom by the person skilled in the art without departing from the protective scope of the present invention.

What is claimed is:

1. A method for moving a patient couch as a function of a body value of a patient positioned on the patient couch for medical imaging, the medical imaging taking place in an imaging modality with a recording region, the patient couch being configured to move within the recording region via a drive chain, and the method comprising:
   providing the body value of the patient;
   setting an operating parameter of the drive chain as a function of the body value such that
      a speed value of the patient couch is increased to an increased speed value, and
      a rocking of the patient couch during movement of the patient couch is at least partially suppressed, the setting being performed via a controller configured to control the drive chain; and
   moving the patient couch via the drive chain in accordance with the increased speed value to perform the medical imaging.

2. The method as claimed in claim 1, further comprising:
   retrieving at least one sequence parameter of an imaging protocol before the setting, the medical imaging being performed in accordance with the imaging protocol, and the setting sets the operating parameter in accordance with the at least one sequence parameter.

3. The method as claimed in claim 2, wherein the at least one sequence parameter corresponds to a movement of the patient couch within the recording region.

4. The method as claimed in claim 3, wherein the movement of the patient couch comprises at least one change in direction.

5. The method as claimed in claim 4, wherein the at least one change in direction amounts to 180°.

6. The method as claimed in claim 2, further comprising:
   entering the body value into a digital twin of the drive chain;
   digitally mapping, by the digital twin, at least one operating state of the drive chain of the patient couch which influences the operating parameter; and
   ascertaining the operating parameter as a function of the body value and the at least one operating state.

7. The method as claimed in claim 1, wherein the setting comprises:
   selecting a motor current characteristic curve of the drive chain as a function of the body value.

8. The method as claimed in claim 7, further comprising:
   entering the body value into a digital twin of the drive chain;
   digitally mapping, by the digital twin, at least one operating state of the drive chain of the patient couch which influences the operating parameter; and
   ascertaining the operating parameter as a function of the body value and the at least one operating state.

9. The method as claimed in claim 1, wherein the speed value corresponds to at least one of an acceleration ramp of the patient couch or a maximum speed of the patient couch.

10. The method as claimed in claim 1, further comprising:
    entering the body value into a digital twin of the drive chain;
    digitally mapping, by the digital twin, at least one operating state of the drive chain of the patient couch which influences the operating parameter; and
    ascertaining the operating parameter as a function of the body value and the at least one operating state.

11. The method as claimed in claim 10, further comprising:
    adapting the at least one operating state to the body value before the ascertaining.

12. The method as claimed in claim 11, further comprising:

adapting the at least one operating state to wear experienced due to movement of the patient couch such that a friction value is increased, the adapting the at least one operating state to wear being performed after the moving.

13. The method as claimed in claim 10, wherein the digital twin is operated in a cloud computing facility.

14. The method as claimed in claim 10, further comprising:
adapting the at least one operating state to wear experienced due to movement of the patient couch such that a friction value is increased, the adapting the at least one operating state to wear being performed after the moving.

15. The method as claimed in claim 1, further comprising: providing, on a display unit of the patient couch, the increased speed value.

16. The method as claimed in claim 1, further comprising: detecting the body value before the patient is positioned on the patient couch.

17. A patient couch for moving a patient positioned on the patient couch, the patient couch comprising:
a couch board configured to position the patient;
a drive chain configured to move the patient couch; and
a controller configured to control the drive chain, wherein the patient couch is configured to perform a method as claimed in claim 1.

18. A non-transitory computer readable storage medium storing computer-executable instructions, which are loadable into a memory of a computing device, wherein the computer-executable instructions cause the computing device to perform a method as claimed in claim 1 when the computer-executable instructions are executed at the computing device.

19. The method of claim 1, wherein the body value includes at least one of a mass of the patient or a physique of the patient.

20. A patient couch for moving a patient positioned on the patient couch, as a function of a body value of the patient, the patient couch comprising:
a couch board configured to position the patient;
a drive chain configured to move the patient couch; and
processing circuitry configured to
set an operating parameter of the drive chain as a function of the body value such that
a speed value of the patient couch is increased to an increased speed value, and
a rocking of the patient couch during movement of the patient couch is at least partially suppressed, and
cause the drive chain to move the patient couch in accordance with the increased speed value to perform medical imaging.

* * * * *